United States Patent [19]

Eliasson et al.

[11] 4,009,187
[45] Feb. 22, 1977

[54] 8-(5-FORMYL-2-FURYL)-OCTANOIC ACID

[75] Inventors: Rune Eliasson, Spanga, Sweden;
Poul Nedenskov, Birkerod, Denmark

[73] Assignee: Aktieselskabet Grindstedvaerket,
Arhus, Denmark

[22] Filed: Mar. 15, 1973

[21] Appl. No.: 341,627

[30] Foreign Application Priority Data

Mar. 20, 1972 United Kingdom ............ 12940/72

[52] U.S. Cl. .............................. 260/347.3; 424/285
[51] Int. Cl.² ....................................... C07D 307/46
[58] Field of Search .......... 260/347.3, 347.4, 347.5

[56] References Cited

OTHER PUBLICATIONS

Fodor et al., Synthesis (9), 464–472 (1972).

*Primary Examiner*—G. Thomas Todd
*Attorney, Agent, or Firm*—Lawrence Rosen; E. Janet Berry

[57] ABSTRACT

This invention relates to novel octanoic acid derivatives of therapeutical value, and to methods for producing the same.

1 Claim, No Drawings

8-(5-FORMYL-2-FURYL)-OCTANOIC ACID

This invention relates to novel octanoic acid derivatives and their preparation.

More particularly, the invention relates to derivatives of the said kind, having the formula:

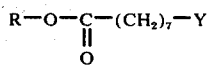   (I)

wherein R is hydrogen or a lower alkyl group, and Y is one of the following groups:

a. a group of the formula:

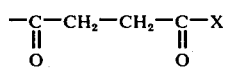   (II)

wherein X is hydrogen, an acetyl group or a group of the formula:

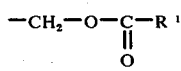   (III)

wherein $R^1$ is a lower alkyl group or a group of the formula:

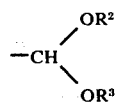   (IV)

wherein each of the groups $R^2$ and $R^3$ is a lower alkyl group or $R^2$ and $R^3$ together is lower alkylene containing at least two carbon atoms, and b. a group of the formula:

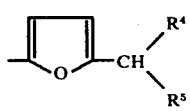   (V)

wherein $R^4$ and $R^5$ together is an oxygen atom or a —O—CH$_2$—CH$_2$—O group, or $R^4$ is hydrogen, when $R^5$ is a hydroxyl group or an acetoxy group.

Some of the compounds of formula I have useful biological properties, whereas others are useful as intermediates, in the production of the former.

The biologically useful compounds have in vitro a.o. an inhibiting effect on the spontaneous motility of the myometrium from non-pregnant women. Thus, they have potential fertility-increasing properties in such cases where the infertility is dependent on too low activity of the prostaglandines in the semen.

Preferred esters are at present the methyl esters.

According to the present invention, the novel compounds are prepared by a process which comprises treating a compound of the general formula

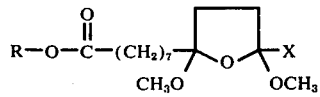

wherein R and X each has the above meaning, with an acid under hydrolyzing conditions. As an example of acids suitable for the purpose according to the invention, mineral acids such as hydrochloric acid and sulphuric acid may be mentioned.

To obtain a high yield of the process compounds, it is of the greatest significance that well defined hydrolyzing conditions should be provided. This can be attained by exactly adjusting the concentration of the hydrolyzing acid, the reaction temperature, and accurately adapting the reaction time. If, for example, the hydrolyzing reaction is carried out in the presence of concentrated hydrochloric acid at room temperature, it must be interrupted within less than 1 minute, to ensure a good result being obtained. If, on the other hand, the hydrolyzing process is carried out in the presence of 1N hydrochloric acid at room temperature, a 30 minutes reaction time is required. Following the hydrolyzing reaction, the reaction product is isolated, e.g. by precipitation or extraction with an organic solvent, and can be purified by crystallization or distillation.

The starting compounds for the reaction as above, which are also novel substances, can be produced by previously known methods, for example by catalytical hydrogenation of compounds having the general formula

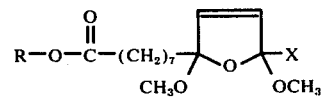

wherein R and X have each the above defined meaning.

These compounds can expediently be prepared by electrolytically oxidizing compounds of the formula

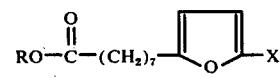

wherein R and X have each the above meanings, in the presence of methanol in a manner known per se.

The compounds of the latter formula, in which X is hydrogen, are formerly known from the literature. The compounds in which X has the above meaning other than hydrogen, can be produced, for example, by formylating compounds of the formula

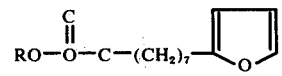

according to Vilsmeier to a compound of the formula

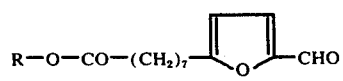

upon which the formyl group is converted into an acetal group by acetalization or into an acyloxymethyl group by reduction to an alcohol group, and acylating the latter.

The novel intermediates also form part of the invention, and some of them have shown activity of the same type as the final compounds.

The following examples are illustrative of compounds of the invention and their preparation.

EXAMPLE 1

13-Acetoxy-9,12-dioxo-tridecanoic methyl ester

A. 8-(2-Furyl)-octanoic acid methyl ester 19 g of 8-(2-furyl)-octanoic acid were refluxed for 4 hours with 100 ml of methanol and 1.5 ml of sulphuric acid. The mixture was then evaporated to one third of its original volume. 100 g. of ice-water were then added, whereupon the mixture was extracted with ether.

The ether extract was washed with an aqueous solution of sodium bicarbonate, and dried. Evaporation and distillation yielded a product having the boiling point 95°–100° C at 0.15 mm Hg.

Analysis: Calculated C, 69.6; H, 9.0; methoxyl, 13.8. Found: C, 69.4; H, 8.8; methoxyl, 13.7%.

B. 8-(5-Formyl-2-furyl)-octanoic acid methyl ester 6.13 g of phosphorous oxychloride were added, while stirring, to 2.93 g of dimethyl formamide at 5°–10° C for 5 minutes. The mixture was kept at 0°–5° C for 40 minutes and then heated to room temperature. Immediately, and with vigorous stirring, 8.96 g of 8-(2-furyl)-octanoic acid methyl ester were added, whereupon the mixture was cooled to 5°–10° C in an ice-salt bath during 1 hour. After further 1 hour at room temperature, 40 g of ice were added, whereupon the mixture was neutralized with 10 g of sodium carbonate. The two phases were then separated, and the aqueous phase was extracted with ether. The combined organic phases were dried and then distilled. Boiling point 144° C at 0.2 mm Hg.

Analysis: Calculated: C, 66.6; H, 8.0; methoxyl, 12.3. Found: C, 66.5; H, 8.0; methoxyl, 12.1%.

C. 8-(5-Acetoxymethyl-2-furyl)-octanoic acid methyl ester 8.22 g of 8-(5-formyl-2-furyl)-octanoic acid methyl ester were dissolved in 100 ml of absolute ethanol, whereupon the solution was cooled to 10° C. 5.0 g. of sodium borohydride (98%) in 100 ml of ethanol were added in one portion while stirring. After 1.5 hours, 10 ml of methanol were added and the solution poured into 150 ml of water. 50 g of potassium carbonate were then added, the temperature being kept below 18° C. The solution was then extracted several times with ether while adding further quantities of potassium carbonate. After drying, the ether was driven off. 10 ml of pyridine were then added to the product, after which the mixture was again dried. The residue was dissolved in 65 ml of pyridine, after which 65 ml of acetic anhydride were added. The mixture was allowed to stand overnight and was then distilled under vacuum. A product having a boiling point of 148°–149° C at 0.2 mm Hg was obtained.

Analysis: Calculated C, 64.8; H, 8.2; O, 27.0. Found: C, 64.8; H, 8.2; O, 27.2%.

D. 8-(5-Acetoxymethyl-2,5-dimethoxy-tetrahydro-2-furyl)-octanoic acid methyl ester.

7.80 g of the compound of step C and 5.00 g of ammonium bromide were dissolved in 270 ml of methanol, whereupon the mixture was electrolyzed at about −16° C according to the method described by Clauson-Kaas et al. in Acta Chemica Scandinavica, vol. 6 (1952), p. 531.

After the electrolyzing process, the reaction mixture was poured into a solution of sodium methoxide in methanol prepared from 1.2 g of sodium metal and 15 ml of methanol.

The solution was concentrated under vacuum on a water bath. 300 ml of ether were then added, after which the solution was filtered, and the ether driven off.

To the resultant oil were added 20 ml of pyridine and 20 ml of acetic anhydride. The mixture was allowed to stand overnight and was then distilled. Boiling point 167°–175° C at 0.1–0.3 mm Hg.

0.4 g of potassium acetate and 8.53 g of the oil were then dissolved in 30 ml of methanol, whereupon the solution was agitated at room temperature with 1 g of Raney-nickel under a hydrogen gas pressure of 100 atmospheres for 17 hours. Filtration and distillation yielded an oil having a boiling point at 163°–168° C at 0.2 mm Hg.

Analysis: Calculated C, 60.0; H, 9.0; O, 31.1; methoxyl, 25.4. Found: C, 60.5; H, 8.8; O, 31.2; methoxyl, 25.1%.

E. 13-Acetoxy-9,12-dioxo-tridecanoic acid methyl ester 6.00 g of the compound of step D were agitated for 40 seconds with 180 ml of concentrated hydrochloric acid. The solution was added rapidly, whilst stirring, to 720 ml of ice-water. The crystalline product was then isolated by filtration, washed with water and dried under vacuum. After recrystallization from ether/petroleum ether, and sublimation at 140° C and 0.2 mm Hg, white crystals were obtained which had a melting point of 64°–65° C.

Analysis: Calculated: C, 61.1; H, 8.3. Found: C, 61.1; H, 8.4%.

EXAMPLE 2

13,13-Dimethoxy-9,12-dioxo-tridecanoic acid methyl ester.

A. 8-(5-Dimethoxymethyl-2-furyl)-octanoic acid methyl ester 32.8 g of 8-(5-formyl-2-furyl)-octanoic acid methyl ester, 15.5 g of trimethyl orthoformate, 16 ml of methanol and 0.3 g of ammonium chloride were mixed and refluxed for 4 hours. The solution was concentrated to dryness on a water bath. The residue was then absorbed in ether, washed with water, dried and distilled. Boiling point 136°–138° C at 0.2 mm Hg.

Analysis: Calculated: C, 64.4; H, 8.8; methoxyl, 31.2. Found: C, 64.8; H, 8.3; methoxyl, 30.1%.

B. 8-(2,5-Dimethoxy-5-dimethoxymethyl-2,5-dihydro-2-furyl)-octanoic acid methyl ester.

12.2 g of the compound of step A (freshly distilled) and 5 g of ammonium bromide were dissolved in methanol and the mixture was then electrolyzed according to the method described in Example 1 D.

Following the electrolyzing process, the mixture was poured into a solution of sodium methoxide in methanol (1.2 g of sodium and 20 ml of methanol). The mixture was then concentrated under vacuum on a water bath, and the residue was dissolved in ether, the solution being filtered and distilled.

Boiling point: 160°–167° C. at 0.15–0.2 mm Hg.

Analysis: Calculated: C, 60.0; H, 9.0; methoxyl, 43.0. Found: C, 60.2; H, 8.9; methoxyl, 42.3%.

C. 8-(2,5-Dimethoxy-5-dimethoxymethyl-tetrahydro-2-furyl)-octanoic acid methyl ester.

8.72 g of the compound of step B, 0.4 g of potassium acetate, 50 ml of methanol, and 2 g of Raney-nickel were agitated under hydrogen gas at a pressure of 100 atmospheres for 17 hours at room temperature. The mixture was then filtered and the methanol was driven off. The residue was dissolved in ether, filtered, concentrated and then distilled.

Boiling point: 166°–178° C at 0.3–0.9 mm Hg.

Analysis: Calculated: C, 59.6; H, 9.5; methoxyl, 42.8. Found: C, 60.1; H, 9.5; methoxyl, 41.3%.

D. 13,13-Dimethoxy-9,12-dioxo-tridecanoic acid methyl ester 24.7 g of the compound of step C were added to 4 liters of 1N hydrochloric acid, after which the mixture was stirred under nitrogen for 25 minutes. The mixture was then extracted several times with ether. The ether solution was washed with an aqueous solution of sodium bicarbonate, dried and concentrated under vacuum, after which the residue was distilled.

Boiling point: 164°–173° C at 0.05 mm Hg. The product contained minor amounts (about 6%) of a by-product, 8-(5-formyl-2-furyl)-octanoic acid methyl ester.

Analysis: Calculated for $C_{16}H_{28}O_6$: C, 60.7; H, 8.9; O, 30.3; methoxyl, 29.4. Found: C, 61.3; H, 8.5; O, 29.7; methoxyl, 28.8%.

EXAMPLE 3

11-Formyl-9-oxo-undecanoic acid methyl ester

A. 8-(2,5-Dimethoxy-2,5-dihydro-2-furyl)-octanoic acid methyl ester.

15.7 g of 8-(2-furyl)-Octanoic acid methyl ester and 5.0 g of ammonium bromide in 270 ml of methanol were electrolyzed at about −12° C by the same method as in Example 1 D. Following the electrolyzing process, the mixture was poured into a solution of sodium methoxide in methanol (1.2 g of sodium and 20 ml of methanol). The solution was concentrated under vacuum on a water bath. Ether was then added, and the solution was filtered, concentrated and distilled under nitrogen.

Boiling point: 128°–236° C at 0.2–0.3 mm Hg.

Analysis: Calculated: C, 62.9; H, 9.2; methoxyl, 32.4. Found: C, 62.8; H, 9.0; methoxyl, 31.7%.

B. 8-(2,5-Dimethoxy-tetrahydro-2-furyl)-octanoic acid methyl ester 31.9 g of the compound of step A, 1.2 g of potassium acetate, 120 ml of methanol and 12 g of Raney-nickel were agitated under hydrogen at a pressure of 100 atmospheres for 3 hours at room temperature. The mixture was then filtered and concentrated, after which the residue was taken up in ether, and the ether solution was filtered, concentrated and distilled.

Boiling point: 125°–128° C at 0.3 mm Hg.

Analysis: Calculated: C, 62.5; H, 9.8; methoxyl, 32.1. Found: C, 62.6; H, 9.8; methoxyl, 32.0%.

C. 11-Formyl-9-oxo-undecanoic acid methyl ester 10.0 g of the compound of step B was stirred for 30 minutes with 2100 ml of 1N hydrochloric acid at room temperature. The mixture was then extracted rapidly several times with ether.

The combined ether extracts were then washed with an aqueous solution of sodium bicarbonate and then with an aqueous solution of sodium chloride, dried, concentrated and distilled.

Boiling point: 144°–150° C at 0.2–0.3 mm Hg.

Analysis: Calculated: C, 64.4; H, 9.2; methoxyl, 12.8. Found: C, 62.7; H, 9.0; methoxyl, 12.7%.

The compound is unstable in air, and the aldehyde group undergoes a rapid oxydation to the corresponding acid.

EXAMPLE 4

8-(5-(1,3-dioxalane)-2-furyl)-octanoic acid methyl ester 8-(5-Formyl-2-furyl)-octanoic acid methyl ester (2.52 g, 0.01 moles), ethyleneglycol (1.24 g, 0.02 moles), benzene (40 ml), and p-toluenesulfonic acid (0.005 g) were stirred and heated under reflux for 1.5 hours with simultaneous azeotropic removal of water. After cooling, the reaction mixture was diluted with benzene (40 ml), washed with 1.5 N sodium hydroxide (60 ml), and then with two portions of water. The benzene solution was dried over magnesium sulfate, after which the solvent was removed from a water bath (100° C) under reduced pressure, at last under 15 mm Hg. The residual yellow oil was purified by distillation giving 2.36 g (80%) of the title compound as a colourless liquid, $b._{0.1}$ 142°–148° C, $n_D^{25}$ 1.4810.

Calculated for $C_{16}H_{24}O_5$ (296.4): C, 64.8; H, 8.2. Found: C, 64.4; H, 8.1%.

EXAMPLE 5

8-(5-Formyl-2-furyl)-octanoic acid 8-(5-Formyl-2-furyl)-octanoic acid methyl ester (5.04 g, 0.02 moles), methanol (30 ml) and 20% aqueous potassium carbonate (55 ml) were stirred and heated under reflux for 40 minutes. The clear solution was concentrated to ⅔ of the volume by distillation from a water bath (50° C) under reduced pressure (100 mm Hg). The residue was washed with ether (30 ml). Ether (50 ml) was added, and the resulting emulsion was acidified to pH 5 with 3N hydrochloric acid. The ethereal layer was separated. The aqueous layer was extracted with ether (30 ml). The combined ethereal extracts were washed with two 50-ml-portions of water and then dried over magnesium sulphate. The dried ethereal solution was evaporated to dryness from a water bath (60° C), at last under 15 mm Hg. The yellow crystalline residue (4.66 g), m.p. 68°–72° C, was crystallized from ethanol-water (1:3). 3.81 g (80%) of the title compound were obtained as pale yellow crystals, m.p. 70°–72° C.

Calculated for $C_{13}H_{18}O_4$ (238.3): C, 65.5; H, 7.6. Found: C, 65.6; H, 7.6%.

EXAMPLE 6

8-(5-Hydroxymethyl-2-furyl)octanoic acid methyl ester 8-(5-Acetoxymethyl-2-furyl)-octanoic acid methyl ester (25.00 g, 0.084 moles), 6% aqueous potassium carbonate (200 g), and methanol (750 ml) were stirred at room temperature for 30 minutes. The solution was concentrated to 1/5 of the volume by distillation from a water bath (40° C) under reduced pressure (60 mm Hg). The residue was diluted with water (400 ml) and extracted with two 500-ml portions of ether. The combined ethereal extracts were washed with water (300 ml) and dried over magnesium sulfate. Evaporation of the solvent from a water bath (60° C) under reduced pressure, at last under 15 mm Hg, left a tea-coloured, oily residue (17.31 g), which after distillation gave 16.30 g (76%) of the title compound, $b_{0.1}$ 141° C, $n_D^{25}$ 1.4815.

Calculated for $C_{14}H_{22}O_4$ (254.3): C, 66.1; H, 8.7. Found: C, 65.7; H, 8.7%.

EXAMPLE 7

13,13-Dimethoxy-9,12-dioxo-tridecanoic acid methyl ester

A. 8-(5-Hydroxymethyl-tetrahydro-2-furyl)-octanoic acid methyl ester

The methyl ester of Example 6 (6.93 g, 0.027 moles), methanol (60 ml) and Raney-nickel (3.0 g) were shaken under 60 atmospheres of hydrogen for 3 hours at 60°–80° C. After filtration, the methanol was distilled from a water bath (65° C) under reduced pressure, at last under 15 mm Hg. The residual colourless oil (6.98 g) was purified by distillation, giving 6.45 g (92%) of 8-(5-hydroxymethyl-tetrahydro-2-furyl)-octanoic acid methyl ester, $b_{0.1}$ 134°–137° C, $n_D^{25}$ 1.4624.

Calculated for $C_{14}H_{26}O_4$ (258.4): C, 65.2; H, 10.1; $OCH_3$, 12.0. Found: C, 65.0; H, 10.0; $OCH_3$, 12.0%

B. 8-(5-Dimethoxymethyl-tetrahydro-2-furyl)-octanoic acid methyl ester 8-(5-Dimethoxymethyl-2-furyl)-octanoic acid methyl ester (6.03 g, 0.02 mol), methanol (50 ml) and Raney nickel (3.0 g) were shaken under 100 atmospheres of hydrogen for 48 hours at 85°–100° C. After filtration, the methanol was distilled under reduced pressure from a water bath (60° C). Ether (50 ml) was added to the residue, and the turbid colourless solution was filtered. The ethereal solution was evaporated to dryness from a water bath under reduced pressure, at last under 15 mm Hg. The residual clear, colourless oil (6.07 g) was purified by distillation from a potassium acetate-coated flask giving 5.66 g (93%) of 8-(5-dimethoxymethyl-tetrahydro-2-furyl)-octanoic acid methyl ester, $b_{0.1}$ 126°–127° C, $n_D^{25}$ 1.4504.

Calculated for $C_{16}H_{30}O_5$ (302.4): C, 63.5; H, 10.0; $OCH_3$, 30.8. Found: C, 63.4; H, 9.9; $OCH_3$, 30.7%.

C. 13,13-Dimethoxy-9,12-dioxo-tridecanoic acid methyl ester 8-(2,5-Dimethoxy-5-dimethoxymethyl-tetrahydro-2-furyl)-octanoic acid methyl ester (1.00 g, 0.0028 mole), 20 ml of acetone and p-toluenesulfonic acid (0.002 g) were stirred for 2 hours at room temperature. The clear solution was poured into cold water (100 ml, 0° C) and extracted with two 50-ml portions of ether. The combined ethereal extracts were washed with 6% aqueous sodium hydrogen carbonate (30 ml) and then with two 50-ml portions of water, dried with magnesium sulfate, and evaporated to dryness from a water bath (60° C), at last under 15 mm Hg. The distillation of residual oil gave 0.83 g (95%) of the title compound, $b_{0.1}$ 154°–156° C, $n_D^{25}$ 1.4531.

Calculated for $C_{16}H_{28}O_6$ (316.4): C, 60.7; H, 8.9; $OCH_3$, 29.4. Found: C, 60.7; H, 8.9; $OCH_3$, 29.4%.

What we claim is:

1. 8-(5-Formyl-2-furyl)-octanoic acid.

* * * * *